United States Patent
Spraul et al.

(10) Patent No.: US 7,518,371 B2
(45) Date of Patent: Apr. 14, 2009

(54) COMPLETELY AUTOMATIC MAS-NMR APPARATUS

(75) Inventors: Manfred Spraul, Ettlingen (DE); Martin Hofmann, Rheinstetten (DE)

(73) Assignee: Bruker Biospin GmbH, Rheinstetten (DE)

( * ) Notice: Subject to any disclaimer, the term of this patent is extended or adjusted under 35 U.S.C. 154(b) by 3 days.

(21) Appl. No.: 11/907,418

(22) Filed: Oct. 12, 2007

(65) Prior Publication Data

US 2008/0088312 A1 Apr. 17, 2008

(30) Foreign Application Priority Data

Oct. 17, 2006 (DE) .................. 10 2006 048 955

(51) Int. Cl.
 *G01V 3/00* (2006.01)
(52) U.S. Cl. ..................................... 324/321
(58) Field of Classification Search .......... 324/300–322
 See application file for complete search history.

(56) References Cited

U.S. PATENT DOCUMENTS

| | | | |
|---|---|---|---|
| 3,681,683 A * | 8/1972 | Huber ....................... 324/321 |
| 4,254,373 A * | 3/1981 | Lippmaa et al. ............. 324/321 |
| 4,511,841 A * | 4/1985 | Bartuska et al. ............. 324/321 |
| 4,859,949 A * | 8/1989 | McKenna ................... 324/321 |
| 5,146,166 A | 9/1992 | Bartuska |
| 5,159,271 A * | 10/1992 | Llor ........................... 324/321 |
| 5,200,702 A | 4/1993 | Lilly |
| 5,236,239 A | 8/1993 | Govang |
| 5,298,864 A * | 3/1994 | Muller et al. ................ 324/321 |
| 5,325,059 A * | 6/1994 | Doty ........................... 324/321 |
| 5,754,048 A * | 5/1998 | Bielecki ..................... 324/321 |
| 7,170,292 B2 * | 1/2007 | Doty et al. .................. 324/321 |
| 7,248,049 B2 | 7/2007 | Volke |
| 7,248,050 B2 | 7/2007 | Hofmann |
| 7,270,783 B2 | 9/2007 | Takase |

* cited by examiner

*Primary Examiner*—Dixomara Vargas
(74) *Attorney, Agent, or Firm*—Paul Vincent

(57) ABSTRACT

A MAS (magic angle spinning) NMR (nuclear magnetic resonance) apparatus, with automatic sample supply by a supply unit (45), is characterized in that an automatic preparation station (44) for samples is provided, with a rotor storage (49) having several rotors (1) for receiving sample material (53) soaked with NMR solution (55), a cap storage (48) with several caps (3), each cap (3) being suited for closing a rotor (1), wherein each cap (3) has a central axial bore (4), several movable pins (5), each being insertable into the central axial bore (4) of a cap (3) to close the bore (4) in the inserted state, a cap handling unit (46*b*) which can grip a cap (3) from the cap storage (48), move it, and dispose it onto a rotor (1), a plunger (61) for inserting a pin (5) into the bore (4) of the cap (3), and a suctioning device (62) for suctioning excess NMR solution (55) that escapes from the bore (4). The apparatus provides simple and automatic preparation of sample units, in particular, closure of rotors with caps.

8 Claims, 5 Drawing Sheets

Fig.1a  Fig.2a  Fig.3a  Fig.3c  Fig.3d  Fig.3e
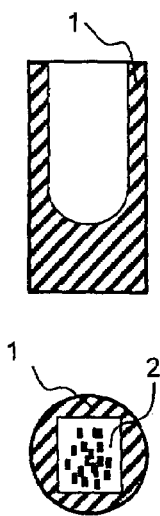
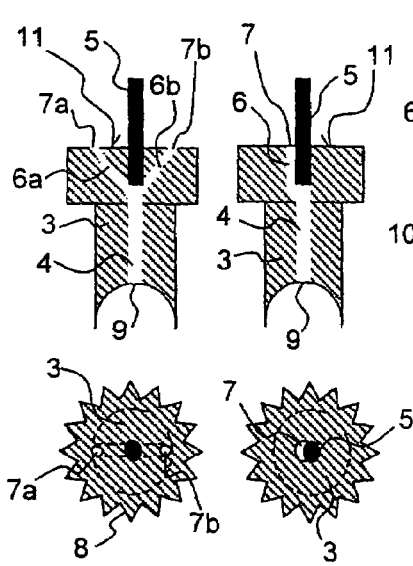
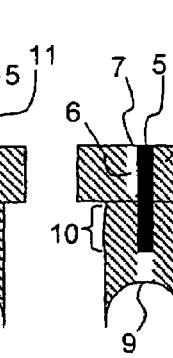
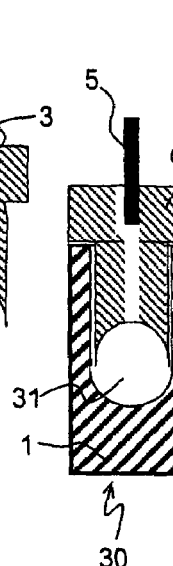
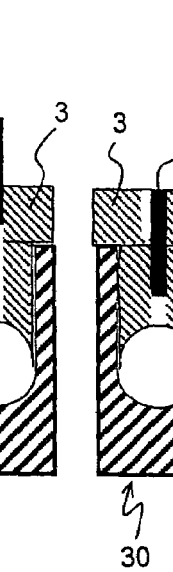
Fig.1b  Fig.2b  Fig.3b

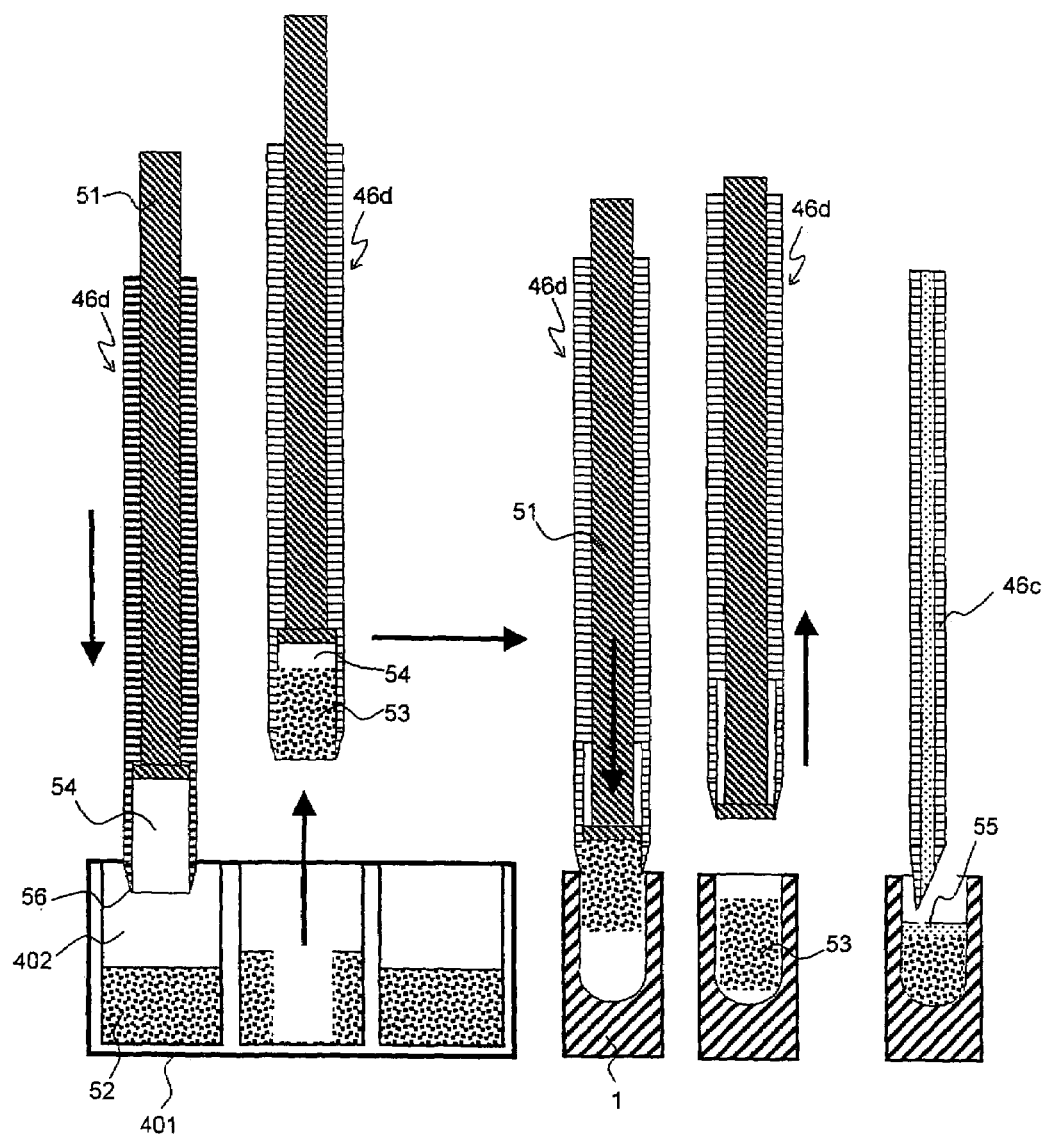

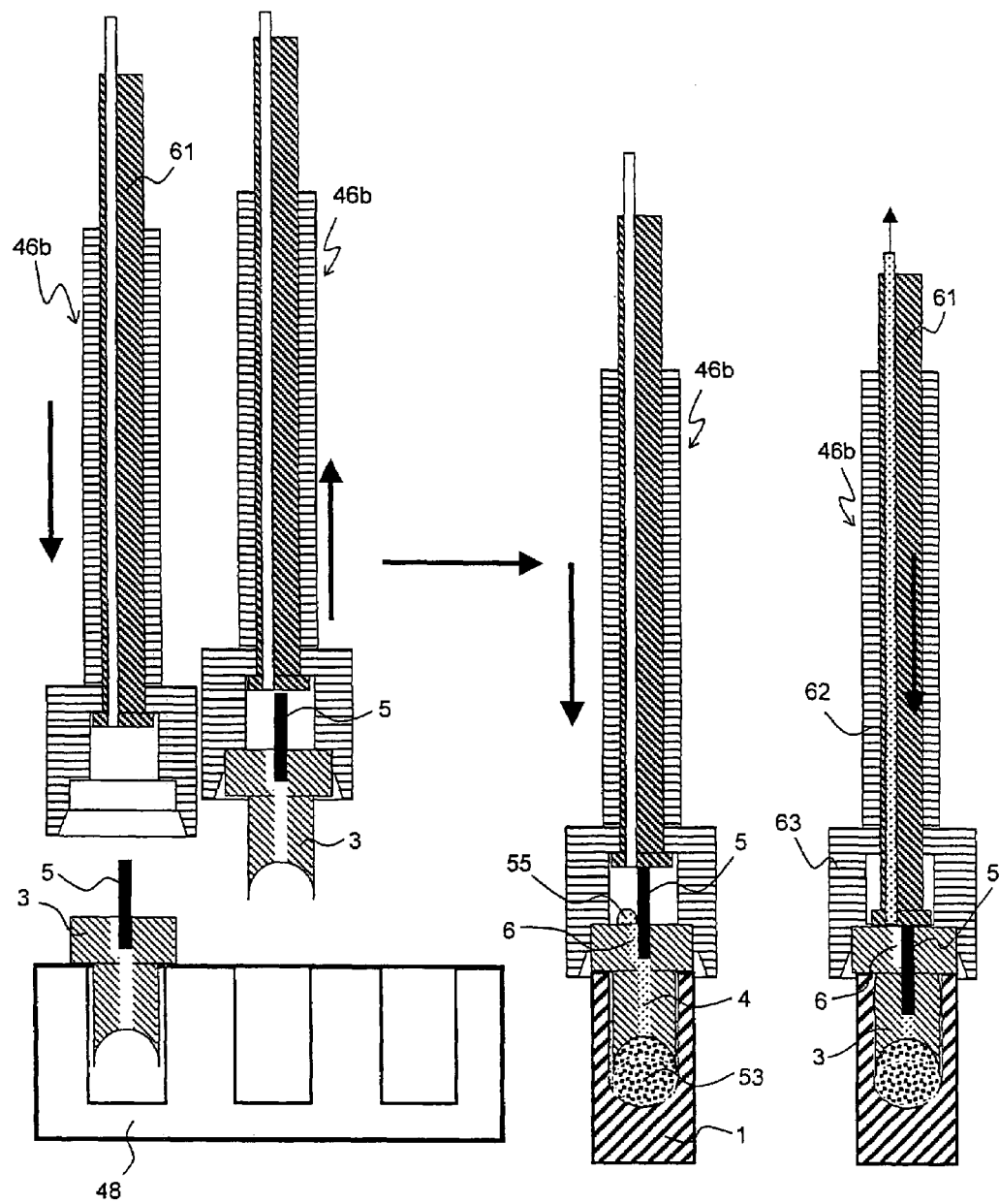

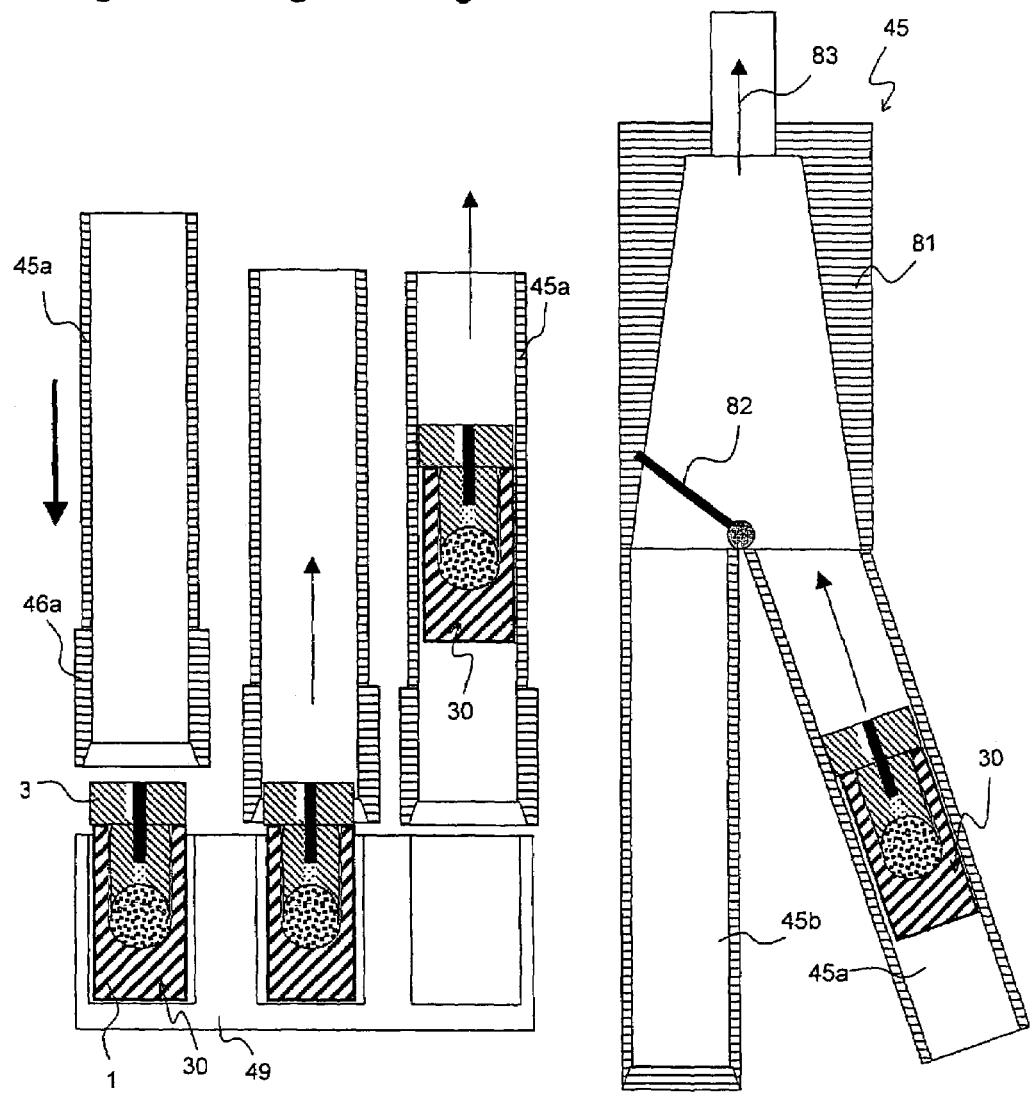

COMPLETELY AUTOMATIC MAS-NMR APPARATUS

This application claims Paris Convention priority of DE 10 2006 048 955.1 filed Oct. 17, 2006 the complete disclosure of which is hereby incorporated by reference.

BACKGROUND OF THE INVENTION

The invention concerns a MAS (magnetic angle spinning) NMR (nuclear magnetic resonance) apparatus, in particular an HR (high resolution) MAS-NMR apparatus, with automatic sample supply by a supply unit.

An apparatus of this type is disclosed in U.S. Pat. No. 5,200,702.

Nuclear magnetic resonance (NMR) spectroscopy is a powerful method of instrumental analytics. Rotation at the magic angle (magic angle spinning (MAS)), which is approximately 54°, has proven to be a useful method for improving the line sharpness in the obtained NMR spectra, in particular, for semisolid samples (semisolids), e.g. tissue samples. HR pulse programs are therefore also suited to measure high-resolution NMR spectra of inhomogeneous samples.

For a MAS measurement, the sample material is loosely disposed in a so-called rotor and soaked with an NMR solution, e.g. $D_2O$. The rotor is substantially a hollow cylinder that is open on one side. A cap tightly closes the rotor. The cap is substantially rotationally symmetric about an axis. The rotor, which is filled with sample material and closed by a cap, is called sample unit herein. The cap has teeth or blades that can move a sample unit, which is located at a measuring position in an NMR spectrometer, into fast rotation using a gas flow. Rotors and caps are disclosed e.g. in U.S. Pat. No. 5,236,239.

Filling sample material into the rotor, soaking the sample material with NMR solution and closing the rotor with the cap is conventionally effected manually. When the rotor is closed, air and excess NMR solution can escape from the interior of the rotor via a central bore in the cap. The bore in the cap is closed by a screw, which is screwed in manually using a screwdriver when the cap is disposed on the rotor. Manual preparation of the sample units is time-consuming and expensive.

U.S. Pat. No. 5,200,702 discloses automatic supply of the readily prepared sample units to a measuring position of an NMR apparatus and measuring thereof. The sample units are thereby disposed in a stacking tube.

It is the underlying purpose of the present invention to present a MAS-NMR apparatus for preparing sample units, in particular, closing the rotors by caps, in a simple and automated fashion.

SUMMARY OF THE INVENTION

This object is achieved by an HR-MAS-NMR apparatus of the above-mentioned type, which is characterized in that an automatic preparation station for samples is provided, comprising:
a) a rotor storage with several rotors for receiving sample material soaked with NMR solution,
b) a cap storage with several caps, wherein each cap is suited to close a rotor and wherein each cap has a central axial bore,
c) several movable pins, each being insertable into the central axial bore of a cap to close the bore in the inserted state,
d) a cap handling unit which
    can grip a cap from the cap storage, move it, and dispose it onto a rotor,
    a plunger for inserting a pin into the bore of the cap, and
    a suctioning device for suctioning excess NMR solution that escapes from the bore.

The inventive NMR apparatus effectively automates closing a rotor with a cap.

The inventive NMR apparatus has a cap storage (e.g. a stack of caps or a rack for a plurality of individual caps) and a rotor storage (e.g. a rotor stack or a rack for a plurality of individual rotors). A cap handling unit can move a cap from the cap storage to a rotor, which is filled with sample material and NMR solution, and dispose it thereon. The rotor may thereby be disposed at a special preparation position (e.g. in a holder or intermediate storage) or at its storage location in the rotor storage. The cap handling unit may thereby be grasped and moved e.g. using a robot arm.

A pin is then pressed into the bore of the cap using the plunger of the cap handling unit to close the cap. The pin expands e.g. the cap in a partial area disposed in the rotor. The elastic cap material clamps the pin and seals it with respect to the rotor. The pin may be removed from a pin storage, or one pin may be pre-assembled on each cap of the cap storage. The closing action by the pin, which is substantially cylindrical (and has, in particular, no outer thread), is particularly easy to automate. The plunger can easily be integrated in the cap-handling unit, such that closure can be effected very quickly, directly after disposing the cap. For this reason, automation is particularly fast.

A suctioning device is also integrated in the cap-handling unit, which can remove the NMR solution, which is displaced from the rotor interior during insertion of the pin. This prevents soiling of the outer area of the sample unit, which could disturb sample supply or falsify NMR measurements.

After the sample unit has been automatically closed, it can be automatically moved, together with the supply unit, to a measuring position.

The inventive NMR apparatus typically comprises an electronic control, which takes over the entire sample preparation, sample supply and generally the administration of the samples.

In one particularly preferred embodiment of an inventive MAS-NMR apparatus, the caps have an overflow channel in the area facing away from the sample, where the suctioning device can act. The overflow channel facilitates escape of the NMR solution from the rotor during closing. In the simplest case, the overflow channel extends parallel to and in contact with the bore for the pin.

In an advantageous further development of this embodiment, the caps each have several overflow channels, which are disposed symmetrically about the axis of rotation of the cap, thereby eliminating any imbalance during rotation of the sample unit during the MAS-NMR measurement.

In another particularly preferred embodiment, the preparation station comprises
    a sample receiver with several sample containers which receive samples, and
    a punching device for punching out sample material from a sample container and transferring it into the interior of a rotor. This embodiment also automates insertion of sample material into the rotor. The punching device retains the sample material after punching out and is moved (e.g. via a robot arm) to the rotor, and then releases the sample material.

In another particularly preferred embodiment, the preparation station comprises a capillary for supplying NMR solution into the interior of a rotor, which permits automation of the supply of NMR solution into the rotor. A robot arm may move the capillary. The NMR solution may be supplied into the rotor before or after insertion of the sample material.

In an advantageous further development of the two above-mentioned embodiments, the capillary is integrated in the punching device, which accelerates automatic sample preparation.

In another preferred embodiment, the supply unit can pneumatically move the rotors, which are filled with soaked sample material and closed by caps, to a measuring position of the apparatus. Pneumatic transport is fast and reliable. The starting position of the sample unit in the preparation station may thereby be the location of sample preparation, a particular holder (intermediate storage), or the storage location in the rotor storage.

In another preferred embodiment, the supply unit is designed to pneumatically move the rotors, which are filled with soaked sample material and closed with caps, to a storage position of the apparatus after termination of the NMR measurement. Pneumatic transport is again quick and reliable. The storage position may be the same as the starting position of the sample unit in the preparation station (this is advisable when the starting position is the storage position in the rotor storage) or the storage position is formed in a particular holder (end storage), preferably in the preparation station.

Further advantages of the invention can be extracted from the description and the drawing. The features mentioned above and below may be used in accordance with the invention either individually or collectively in arbitrary combination. The embodiments shown and described are not to be understood as exhaustive enumeration but have exemplary character for describing the invention.

The invention is shown in the drawing and is explained in more detail by means of embodiments.

BRIEF DESCRIPTION OF THE DRAWING

FIG. 1a shows a schematic cross-sectional view of a rotor for use with the invention;

FIG. 1b shows a schematic view from below of the rotor of FIG. 1a;

FIG. 2a shows a schematic cross-sectional view of a cap in accordance with the invention, with two symmetric overflow channels and pre-assembled extended pin;

FIG. 2b shows a schematic top view of the cap of FIG. 2a;

FIG. 3a shows a schematic cross-sectional view of a cap in accordance with the invention, with an overflow channel parallel to the bore and with pre-assembled extended pin;

FIG. 3b shows a schematic top view of the cap of FIG. 3a;

FIG. 3c shows the cap of FIG. 3a with inserted pin;

FIG. 3d shows a schematic cross-sectional view of a sample unit in accordance with the invention, comprising the rotor of FIG. 1a and the cap of FIG. 3a, in the unclosed state;

FIG. 3e shows the sample unit of FIG. 3d in the closed state;

FIG. 5a shows a cross-sectional view of the sample storage for sample containers and a punching device in accordance with the invention;

FIG. 5b shows the punching device of FIG. 5a with punched-out sample material;

FIG. 5c shows the punching device of FIG. 5b during filling the sample material into a rotor;

FIG. 5d shows the punching device and the rotor of FIG. 5c after filling the sample material into the rotor;

FIG. 5e shows the rotor of FIG. 5d during filling-in NMR solution using a capillary;

FIG. 6a shows a schematic cross-sectional view of a cap in a cap storage and a cap-handling unit in accordance with the invention;

FIG. 6b shows the cap-handling unit of FIG. 6a with grasped cap;

FIG. 6c shows the cap handling unit and the cap of FIG. 6b after disposing the cap onto a rotor;

FIG. 6d shows the cap handling unit, the cap, and the rotor of FIG. 6c after inserting the pin;

FIG. 7a shows a schematic cross-sectional view of the prepared, closed sample unit in a rotor storage and the front part of a supply unit in accordance with the invention before the sample unit is gripped;

FIG. 7b shows the sample unit and the front part of the supply unit in accordance with FIG. 7a during suctioning of the sample unit;

FIG. 7c shows the sample unit and the front part of the supply unit in accordance with FIG. 7b, during pneumatic transport of the sample unit;

FIG. 8 shows a schematic cross-sectional view of a pneumatic supply unit in the area of a switch with prepared sample unit in accordance with the invention.

DESCRIPTION OF THE PREFERRED EMBODIMENT

Figure 4:
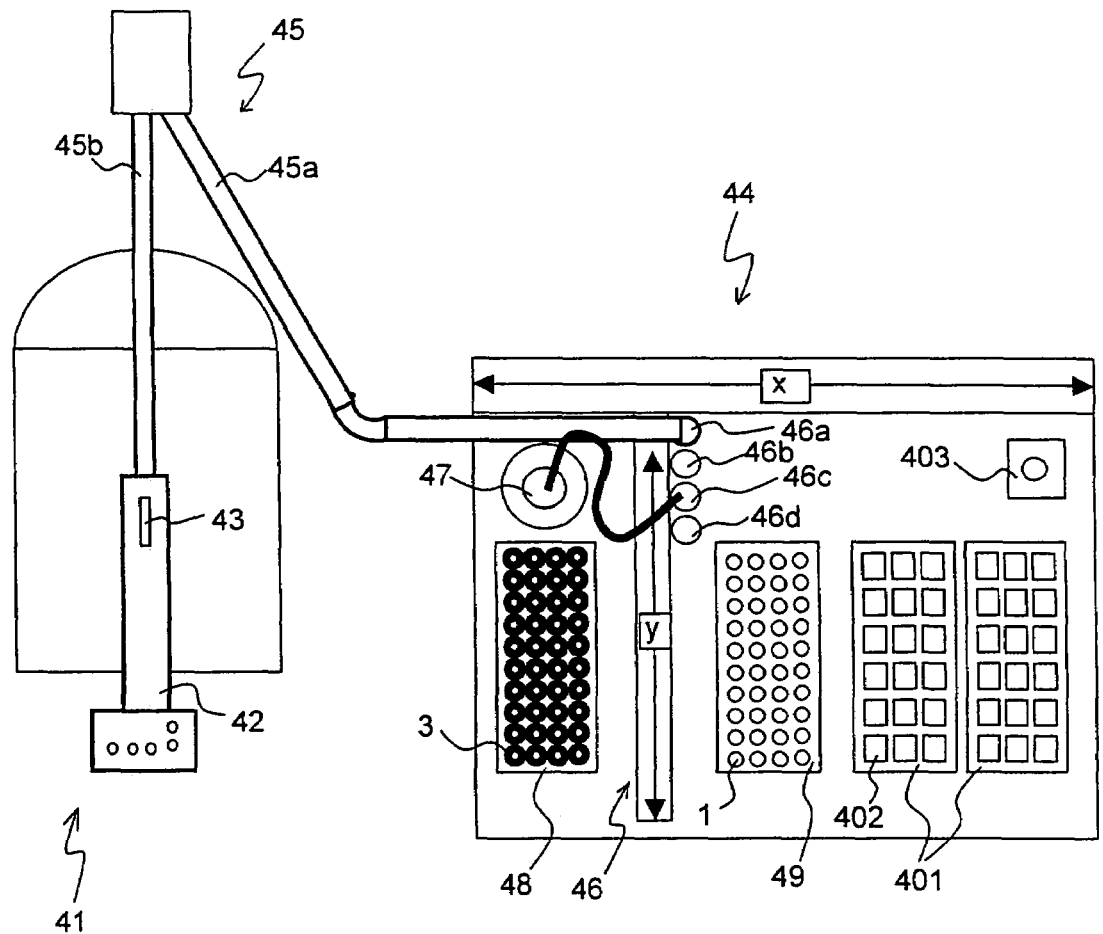
FIG. 4 shows a schematic structure of an inventive HR-MAS-NMR apparatus with preparation station, supply unit and NMR spectrometer.

The present invention fully automates the measuring procedure in a MAS-NMR apparatus, including sample preparation, sample transport and storage of rotors.

In accordance with prior art, the sample containers (rotors), which are used in a MAS measurement, are manually filled with sample material and the rotors are also manually filled with NMR solution (lock solvent). Closing of the rotors with a cap and feeding a sample magazine provided on the NMR spectrometer are also effected manually. This is due to the small rotor dimensions and the precision-mechanical closing mechanisms of the rotor caps.

The invention proposes to provide the NMR apparatus with a suitable automatic preparation station, the use of which would omit manual steps. Special inventive rotors, caps, and a cap-handling unit, which are particularly suited for automation, are used at the preparation station.

FIG. 1a shows a cross-section of a rotor 1 which can be used in the invention. The rotor 1 is designed as a hollow cylinder, which is open on one side. The rotor 1 receives sample material that has been soaked with NMR solution. It can be rotated approximately without imbalance about a central axis, which extends perpendicularly in FIG. 1a. A two-dimensional matrix code 2 can be provided at the bottom of the rotor 1 (FIG. 1b) for identification. In the example shown, the rotor 1 has a round outer cross-section, but also non-spherical, e.g. polygonal, outer cross-sections are feasible. The rotor 1 moreover has a circular inner cross-section. The rotor 1 may e.g. be produced from glass.

FIG. 2a shows a cross-section of a first embodiment of a cap 3 for use with the invention. The cap 3 has a continuous central axial bore 4 in which a pin 5 is displaceably disposed. The pin 5 projects past the cap 3 at the upper end facing away from the sample. In this state, the cap 3 is not closed since the bore 4 is connected, below the pin 5, to the upper side 11 of the cap 3 facing away from the sample via two overflow channels 6a, 6b. The two overflow channels 6a, 6b are disposed mirror-symmetrically relative to the bore 4. The lower part of the cap 3, which faces the sample material in the assembled state, is spherically curved in the embodiment shown. The bore 4 has an opening 9 in the curved lower part. The lower part of the cap 3 has a circular outer cross-section, wherein the diameter is slightly smaller than the inner diameter of the associated rotor (see also FIG. 3d).

The top view of FIG. 2b of the cap 3 also shows the upper openings 7a, 7b of the overflow channels 6a, 6b. The upper part of the cap 3 has teeth or blades 8 on which a gas flow can act in order to rotate a closed sample unit during measurement (typically with 2,000-15,000 revolutions per second). The cap 3 can also rotate about its center axis substantially without imbalance due to its high symmetry (in FIG. 2a extending perpendicularly in the center of the bore 4).

FIG. 3a shows a cross-sectional view of another embodiment of a cap 3. In this embodiment, an overflow channel 6 extends slightly eccentrically (laterally) to the central axial bore 4. The slight imbalance close to the axis has no negative effect in practice. In the illustrated unclosed state of the pin 5, the opening 9 facing the sample and the upper side 11 of the cap 3 facing away from the sample are connected via the lower part of the bore 4 and the overflow channel 6. The top view of FIG. 3b also shows the opening 7 of the overflow channel. The overflow channel 6 narrows on the border to the bore 4 or pin 5, such that the pin 5 is safely guided in the bore 4 and cannot slip into the overflow channel 6.

FIG. 3c shows the cap 3 of FIG. 3a in the closed state, i.e. with inserted pin 5. The pin 5 thereby projects more deeply into the bore 4 than the overflow channel 6 projects into the cap 3. The pin 5 therefore blocks the connection between opening 9 of the bore and the opening 7 of the overflow channel. In a central section 10 of the cap 3, the bore 4 is slightly narrower than the diameter of the pin 5 such that the cap 3 is elastically expanded. Suitable cap materials are e.g. Teflon® or Kel-F® which have sufficient elastic deformation properties.

FIG. 3d shows a sample unit 30 comprising a rotor 1 with disposed cap 3 in the unclosed state. The lower part of the cap 3 and the inner bottom of the rotor 1 delimit a measuring space 31 in the sample unit 30, which has an approximately spherical shape (a shaped body may alternatively be provided on a straight inner bottom of the rotor 1, which is spherically curved). The spherical shape prevents magnetic field distortions during an NMR measurement. The measuring space 31 is provided for receiving sample material and NMR solution (not shown for reasons of simplicity). The sample unit 30 of FIG. 3e is closed, i.e. the pin 5 is inserted. The expanded cap 3 tightly abuts the inner wall of the rotor 1 in an annular area 32. The closure is designed such that the fast rotation that acts on the rotor 1 during the measurement does not cause any leakage.

FIG. 4 shows an inventive NMR apparatus comprising an NMR spectrometer 41 with a high-resolution magic-angle spinning probe head 42 which has a measuring position 43 for a sample unit and moreover a preparation station 44 and a supply unit 45 for transferring sample units from the preparation station 44 to the measuring position 43 (and typically also back).

The preparation station 44 has a preparation robot 46 which can be displaced in three orthogonal directions x, y, and z (z perpendicular to the plane of the drawing), and, in this embodiment, can handle four different tools 46a to 46d using a holder (not shown). The tools are the front end 46d (suction pipe opening) of a transfer tube 45a of the pneumatic supply unit 45 (see also FIG. 7a),
a cap handling unit 46b (see also FIG. 5a),
a capillary 46c or needle for NMR solvents, which is connected to an NMR solvent supply 47,
and a punching device 46d (see also FIG. 6a).

The preparation station 44 moreover comprises a cap storage 48, which is designed in the present case as a rack for a plurality of individually disposed identical caps 3. Each cap 3 has a pre-assembled pin in the unclosed state. A rotor storage 49 is also part of the preparation station 44. The rotor storage 49 is also designed as a rack for a plurality of individually disposed, identical open rotors 1. The rotor storage 49 of the shown embodiment serves to prepare samples (filling and closing the rotors) and also to store readily prepared sample units before and after NMR measurements. Moreover, two sample receivers 401 are provided in which a plurality of sample containers 402 are disposed next to each other. Each sample container 402 contains a tissue sample, some sample material of which is to be measured using NMR. The preparation station 44 also comprises a read station 403 for bar codes, matrix codes, RFID or the like to uniquely identify rotors 1 or sample units.

All positions of caps 3 in the cap storage 48, rotors 1 in the rotor storage 49, sample containers 402 in the sample receivers 401 and the read station 403 are in the working region of the preparation robot 46.

A washing station (not shown) may additionally be provided in the working area of the preparation station to clean the tools and to avoid mutual soiling of samples. Intermediate storages or end storages for sample units or rotors may furthermore be provided in the preparation station of other embodiments (not shown), as well as a gripping tool for sample units or rotors for transfer within the preparation station. A tool may be omitted by integrating several functions in one tool (e.g. punching device and capillary).

The preparation proceedings at the preparation station 44 are described below:

In a first work step, illustrated by FIGS. 5a to 5d, a piece of sample material is removed from the sample support by the punching device 46d, and inserted into a rotor 1.

Towards this end, the punching device 46d is initially moved in the xy plane over a sample container 402 of the sample receiver 401 using a retracted mechanical slider 51 (FIG. 5a). The punching device 46d is then lowered in the z direction and an annular cutting edge 56 penetrates into a tissue sample 52 which is disposed in the sample container 402 and separates a piece of sample material 53 (suitable samples 52 are i.a. human, animal and vegetal tissue, in particular, skin, organs, fruit flesh or leaves, but also complete living beings, such as worms). The punching device 46d is withdrawn upwardly, wherein the sample material 53 remains in the punch opening 54 (FIG. 5b). The punching device 46d is subsequently moved via a rotor 1 and the mechanical slider 51 is moved downwards, such that the sample material 53 is ejected (FIG. 5c). The shape of the punched-out piece of sample material 53 exactly fits into the rotor 1. The punching device 46d is then withdrawn (FIG. 5d). Alternatively, the sample piece may also be pneumatically ejected (instead of the mechanical slider (not shown)).

In a subsequent second work step, the interior of the rotor 1 is filled with NMR solution (lock solvent) 55 (e.g. $D_2O$) by means of the capillary 46c (see FIG. 5e). In accordance with the invention, the rotor 1 may alternatively be filled first with NMR solution (receiver of the NMR solution), and the sample material is subsequently filled into the rotor (not shown).

In a third work step, illustrated in FIGS. 6a to 6d, a cap 3 is disposed onto the rotor 1 and closed.

The cap handling unit 46b is moved over a cap 3 located in the cap storage 48. The cap 3 has a pre-assembled closure pin 5, which projects past the cap 3 (unclosed state). With the punch 61 withdrawn, the cap handling unit 46b is lowered onto the cap 3 in the z direction (FIG. 6a). After gripping the cap 3 with clamps (not shown), with the pin 5 remaining in the open state, the cap handling unit 46b is withdrawn (FIG. 6b) and moved over a rotor 1 which already contains sample material 53 and NMR solution 55. The cap handling unit 46b is subsequently lowered, wherein the cap 3 is inserted into the rotor 1 (FIG. 6c). The sample material 53 is thereby typically somewhat compressed and NMR solvent 55 escapes through the bore 4 and the overflow channel 6 on the upper side of the cap 3. The pin 5 is then (FIG. 6d) pressed into the cap 3 towards the sample (or the sample material 53) using the plunger 61, wherein more NMR solvent 55 escapes via the overflow channel 6 (without the overflow channel it would hardly be possible to press-in the pin, due to the incompressibility of the NMR solution). The escaping NMR solvent 55 is suctioned via a suctioning device 62, which is integrated in the plunger 61 in the embodiment shown. The suctioning draught can be provided via the recesses on the closing cap 3 or through a small lateral bore 63 in the cap handling unit 46b. The cap handling unit 46b can subsequently be retracted (not shown).

In the fourth step, the sample unit 30, i.e. the readily prepared rotor 1 which is closed by a cap 3 is subsequently pneumatically transferred to the measuring position in the NMR spectrometer (see FIGS. 7a-7c and 8). Towards this end, the front-end 46a of the transfer hose 45a is moved over the sample unit 30 (FIG. 7a), lowered (FIG. 7b) and the sample unit 30 is suctioned (FIG. 7c). The sample unit 30 is subsequently moved in the transfer hose 45a. A switch 81 is moreover provided in the supply unit 45, (FIG. 8) in which the sample unit 30 can be held, such that the direction of motion or the transfer hose can be changed with a flap 82, i.e. from the transfer hose 45a which leads to the preparation station, to the transfer hose 45b which leads to the measuring position in the NMR probe head. During turning, the position of the sample unit 30 relative to the suctioning direction 83 also changes. The switch 81 is typically disposed over the magnet of the NMR spectrometer.

It is also possible to use a rotatable plate with holding positions for several sample units (not shown) instead of a switch with flap.

After the measurement, the supply unit 45 steps are reversed. The sample unit 30 is returned from the measuring position to the switch 81 and is either returned to its original initial position or moved to a new storage location.

We claim:

1. A MAS (magic angle spinning) NMR (nuclear magnetic resonance) apparatus or a HR (high resolution) MAS-NMR apparatus with automatic sample supply by a supply unit of an automatic sample preparation station, the apparatus comprising:
    a rotor storage structured to accommodate several rotors for receiving sample material soaked with NMR solution;
    a cap storage structured to accommodate several caps, wherein each cap is suited for closing a rotor, each cap having a central axial bore;
    means for accommodating several movable pins, each pin being insertable into the central axial bore of a cap to close the bore in an inserted state; and
    a cap handling unit having means for gripping a cap from said cap storage and for disposing the cap onto a rotor, a plunger for inserting a pin into the bore of a cap, and a suctioning device for suctioning excess NMR solution that escapes from the bore.

2. The MAS-NMR apparatus of claim 1, wherein the caps have an overflow channel in an area facing away from the sample, on which said suctioning device can act.

3. The MAS-NMR apparatus of claim 2, wherein each cap has several overflow channels which are disposed symmetrically about an axis of rotation of the cap.

4. The MAS-NMR apparatus of claim 1, further comprising a sample receiver with several sample containers which receive samples, and a punching device for punching out sample material from a sample container and moving the sample material into an interior of a rotor.

5. The MAS-NMR apparatus of claim 4, further comprising a capillary for feeding NMR solution into an interior of a rotor.

6. The MAS-NMR apparatus of claim 5, wherein said the capillary is integrated in said punching device.

7. The MAS-NMR apparatus of claim 1, further comprising means for pneumatically moving rotors, filled with soaked sample material and closed by caps, to a measuring position of the apparatus.

8. The MAS-NMR apparatus of claim 1, further comprising means for pneumatically moving rotor, filled with soaked sample material and closed by caps, to a storage position of the apparatus after termination of an NMR measurement.

* * * * *